US011821000B2

(12) United States Patent
Cook et al.

(10) Patent No.: US 11,821,000 B2
(45) Date of Patent: Nov. 21, 2023

(54) METHOD OF SEPARATING VIRAL VECTORS

(71) Applicant: DIONEX CORPORATION, Sunnyvale, CA (US)

(72) Inventors: Kenneth George Cook, Nothumberland (GB); Alexander Boris Schwahn, Basel (CH); Jung Un Baek, San Jose, CA (US); Shanhua Lin Liehr, Palo Alto, CA (US)

(73) Assignee: Dionex Corporation, Sunnyvale, CA (US)

(*) Notice: Subject to any disclaimer, the term of this patent is extended or adjusted under 35 U.S.C. 154(b) by 413 days.

(21) Appl. No.: 17/094,522

(22) Filed: Nov. 10, 2020

(65) Prior Publication Data

US 2022/0145324 A1    May 12, 2022

(51) Int. Cl.
| | |
|---|---|
| *C12N 7/02* | (2006.01) |
| *C12N 15/864* | (2006.01) |
| *C12N 7/00* | (2006.01) |
| *G01N 30/02* | (2006.01) |
| *G01N 30/62* | (2006.01) |
| *C12N 15/86* | (2006.01) |
| *G01N 30/72* | (2006.01) |
| *G01N 30/86* | (2006.01) |

(52) U.S. Cl.
CPC ............ *C12N 15/86* (2013.01); *C12N 7/00* (2013.01); *G01N 30/7233* (2013.01); *G01N 30/86* (2013.01); *G01N 2030/027* (2013.01)

(58) Field of Classification Search
None
See application file for complete search history.

(56) References Cited

U.S. PATENT DOCUMENTS

| | | |
|---|---|---|
| 7,261,544 B2 | 8/2007 | Qu et al. |
| 8,137,948 B2 | 3/2012 | Qu et al. |
| 9,528,126 B2 | 12/2016 | Qu et al. |
| 9,809,639 B2 | 11/2017 | Gagnon |
| 9,868,762 B2 | 1/2018 | Demina et al. |
| 2018/0163183 A1 | 6/2018 | Brument |
| 2020/0284771 A1 | 9/2020 | Wang et al. |
| 2021/0009964 A1 | 1/2021 | Khatwani et al. |

FOREIGN PATENT DOCUMENTS

WO    20170100676 A1    6/2017

OTHER PUBLICATIONS

Dickerson et al, Separating Empty and Full Recombinant Adeno-AssociatedVirus Particles Using Isocratic Anion Exchange Chromatography, Biotechnol. J. 2021, pp. 1-9.*
Santoshkumar et al, Anion-exchange HPLC assay for separation and quantification of empty and full capsids in multiple adeno-associated virus serotypes, Molecular Therapy: Methods & Clinical Development vol. 21 Jun. 2021, pp. 548-558.*
Qu et al, Separation of adeno-associated virus type 2 empty particles from genome containing vectors by anion-exchange column chromatography, Journal of Virological Methods 140 (2007) 183-192.*
Füssl F, et al., "Charge Variant Analysis of Monoclonal Antibodies Using Direct Coupled pH Gradient Cation Exchange Chromatography to High-Resolution Native Mass Spectrometry", Analytical Chemistry, 2018, vol. 90, pp. 4669-4676.
Füssl F, et al., "Comprehensive characterisation of the heterogeneity of adalimumab via charge variant analysis hyphenated on-line to native high resolution Orbitrap mass spectrometry", MABS, 2019, vol. 11, No. 1, pp. 116-128.
Füssl F, et al., "Cracking Proteoform Complexity of Ovalbumin with Anion-Exchange Chromatography-High-Resolution Mass Spectrometry under Native Conditions", Journal of Proteome Research, 2019, vol. 18, pp. 3689-3702.
Qu G, et al., "Separation of adeno-associated virus type 2 empty particles from genome containing vectors by anion-exchange column chromatography", Journal of Virological Methods, 2007, vol. 140, pp. 183-192.
Qu W, et al., "Scalable Downstream Strategies for Purification of Recombinant Adeno-Associated Virus Vectors in Light of the Properties", Current Pharmaceutical Biotechnology, 2015, vol. 16, pp. 684-695.
Wang C, et al., "Developing an Anion Exchange Chromatography Assay for Determining Empty and Full Capsid Contents in AAV6. 2", Molecular Therapy Methods & Clinical Development, 2019, vol. 15, pp. 257-263.
Shan L. et al. "Gradient Chromatofocusing-Mass Spectrometry: A New Technique in Protein Analysis," Journal of the American Society for Mass Spectrometry, Aug. 1, 2008, vol. 18, No. 8, pp. 1132-1137.
Addgene: "Adeno-associated Virus (AAV) Guide," Retrieved on Apr. 3, 2023, 3 pages, Retrieved from the internet URL: https://www.addgene.org/guides/aav/.
Thermo Scientific: "Ion Exchange Chromatography," Pierce Biotechnology, 2 pages.
Tokmakov A.A., et al., "Protein pI and Intracellular Localization," Frontiers in Molecular Biosciences, Nov. 29, 2021, vol. 8, pp. 1-6.
Yang H, et al., "Anion-Exchange Chromatography for Determining Empty and Full Capsid Contents in Adeno-Associated Virus", Waters Corporation, Milford, MA, 2020, pp. 1-7.

* cited by examiner

*Primary Examiner* — Maria Marvich (57) ABSTRACT

A method of separating a liquid sample containing viral vectors includes flowing the liquid sample into an anion exchange column. A first viral vector contains a targeted genetic material and a second viral vector contains essentially no genetic material or a non-targeted genetic material, wherein the targeted genetic material is different than the non-targeted genetic material. A mobile phase can be flowed into the anion exchange column, wherein the mobile phase includes a buffer solution A and a buffer solution B. The buffer solutions A and B both include volatile buffer salts. The first viral vector and the second viral vector can be separated so that the first viral vector and the second viral vector elute off the anion exchange column at different times and then be detected.

11 Claims, 5 Drawing Sheets

METHOD OF SEPARATING VIRAL VECTORS

BACKGROUND

Ion exchange chromatography (IEC) is a widely used analytical technique for the chemical analysis and separation of charged molecules. IEC involves the separation of one or more analyte species from other matrix component present in a sample. The analytes are typically ionic so that they can have an ionic interaction with a stationary phase. In IEC, the stationary phase is derivatized with ionic moieties that ideally will interact with the analytes and matrix components with varying levels of affinity. When using a salt gradient elution, an eluent is percolated through the stationary phase and competes with the analyte and matrix components for interacting with the ionic moieties. When using a pH gradient elution, the pH of the eluent modifies the charge of the analyte and in turn changes the binding of the analyte to the stationary phase. For reference, the eluent is a term used to describe a liquid solution or buffer solution that is pumped into a chromatography column inlet. During the elution process, the analyte and matrix components will elute off the stationary phase as a function of time and then be subsequently detected at a detector. Examples of some typical detectors are a conductivity detector, a UV-VIS spectrophotometer, and a mass spectrometer. Over the years, IEC has developed into a powerful analytical tool that is useful for creating a healthier, cleaner, and safer environment where complex sample mixtures can be separated and analyzed for various industries such as water quality, environmental monitoring, food analysis, pharmaceutical, and biotechnology.

Gene therapy using viral vectors is a rapidly emerging field, with many treatments in development and several recent FDA approvals. Recombinant viral vectors can be used to encapsulate and deliver genomic material into a patient's cells to treat a disease. Ideally, the final product consists of viral vector particles that all contain the therapeutic genetic material. However due to low packaging efficiency or ejection of the genomic material during processing and storage, viral vectors do not always contain the desired genetic material (e.g., DNA molecule). These empty viral particles compete for the same cellular receptors while possessing no therapeutic function. Applicant believes that there is a need to develop a method that can characterize a batch of viral vectors to determine the yield of the vectors containing genetic material compared to vectors that either do not contain targeted genetic material or contain non-targeted genetic material (e.g., wrong genetic material or a truncated version of the targeted genetic material). Further, Applicant believes that there is a need to develop a method for characterizing a batch of viral vectors with a workflow that is compatible with mass spectrometry.

SUMMARY

In a first aspect of a method of separating a liquid sample containing viral vectors includes flowing the liquid sample into an anion exchange column. The viral vectors include a first viral vector and a second viral vector. The first viral vector contains a targeted genetic material. The second viral vector contains i) essentially no genetic material or ii) a non-targeted genetic material. The targeted genetic material is different than the non-targeted genetic material. A mobile phase can be flowed into the anion exchange column, wherein the mobile phase includes a mixture of a first buffer solution A and a second buffer solution B. The first buffer solution A includes ammonium bicarbonate and ammonium hydroxide. The second buffer solution B includes acetic acid and formic acid. The first viral vector and the second viral vector are separated so that the first viral vector and the second viral vector elute off the anion exchange column at different times. The first viral vector and the second viral vector are detected with a detector.

In regard to any of the first aspects, the first buffer solution A and the second buffer solution B, each do not include non-volatile buffer salts dissolved in the liquid.

In regard to any of the first aspects, the flowing of the mobile phase into the anion exchange column includes pumping the first buffer solution A from a first reservoir, wherein the first buffer solution A has a first pH value. The second buffer solution B can be pumped from a second reservoir, wherein the second buffer solution B has a second pH value and that that the first pH and the second pH are different. The pumped first buffer solution A and the pumped second buffer solution B can be combined to form the mixture of the first buffer solution A and the second buffer solution B before inputting the mixture into an anion exchange column. A proportion of the first buffer solution A and the second buffer solution B can be varied for the combined solution as a function of time.

In regard to any of the first aspects, the combining the pumped first buffer solution A and the pumped second buffer solution B includes mixing the pumped first buffer solution A and the pumped second buffer solution B in a mixer before the pumped first buffer solution A and the pumped second buffer solution B are flowed into the anion exchange column.

In a second aspect of a method of separating a liquid sample containing viral vectors, it includes flowing the liquid sample into an anion exchange column. The viral vectors include a first viral vector and a second viral vector. The first viral vector contains a targeted genetic material. The second viral vector contains i) essentially no genetic material or ii) a non-targeted genetic material, wherein the targeted genetic material is different than the non-targeted genetic material. A mobile phase can be flowed into the anion exchange column, wherein the flowing the mobile phase further includes pumping the first buffer solution A from a first reservoir. The first buffer solution A includes ammonium bicarbonate. The second buffer solution B can be pumped from a second reservoir, wherein the second buffer solution B includes ammonium hydroxide. The third buffer solution C can be pumped from a third reservoir, wherein the third buffer solution C includes acetic acid. The fourth buffer solution D from a fourth reservoir, wherein the third buffer solution D includes formic acid. The pumped first buffer solution A, the pumped second buffer solution B, the pumped third buffer solution C, the pumped fourth buffer solution D can be combined to form a mixture before inputting the mixture into the anion exchange column. A proportion for each of the first buffer solution A, the second buffer solution B, the third buffer solution C, and the fourth buffer solution D can be controlled as a function of time. The first viral vector and the second viral vector can be separated so that the first viral vector and the second viral vector elute off the anion exchange column at different times. The first viral vector and the second viral vector can be detected with a detector.

In regard to the any of the second aspects, the controlling the proportion for each of the first buffer solution A, the second buffer solution B, the third buffer solution C, and the fourth buffer solution D can be controlled as a function of time to form a pH gradient.

In regard to any of the second aspects, the first buffer solution A, the second buffer solution B, the third buffer solution C, and the fourth buffer solution D each do not include non-volatile buffer salts dissolved in the liquid.

In regard to any of the second aspects, the combining the first buffer solution A, the second buffer solution B, the third buffer solution C, and the fourth buffer solution D includes mixing the first buffer solution A, the second buffer solution B, the third buffer solution C, and the fourth buffer solution D in a mixer before the first buffer solution A, the second buffer solution B, the third buffer solution C, and the fourth buffer solution D are flowed into the anion exchange column.

In a third aspect of a method of separating a liquid sample containing viral vectors, it includes flowing the liquid sample into an anion exchange column. The viral vectors include a first viral vector and a second viral vector. The first viral vector contains a targeted genetic material. The second viral vector contains i) essentially no genetic material or ii) a non-targeted genetic material, wherein the targeted genetic material is different than the non-targeted genetic material. A mobile phase can be flowed into the anion exchange column, wherein the flowing the mobile phase further includes pumping the first buffer solution A from a first reservoir. The second buffer can be pumped from solution B from a second reservoir. The third buffer solution C can be pumped from a third reservoir. The pumped first buffer solution A, the pumped second buffer solution B, and the pumped third buffer solution C can be combined to form a mixture before inputting the mixture into the anion exchange column. A proportion for each of the first buffer solution A, the second buffer solution B, and the third buffer solution C can be controlled as a function of time. The first buffer solution A contains a buffer component selected from the group consisting of ammonium bicarbonate, ammonium hydroxide, formic acid, and acetic acid. The second buffer solution B contains a buffer component selected from the group consisting of ammonium bicarbonate, ammonium hydroxide, formic acid, and acetic acid. The first buffer solution A has a different buffer component than the second buffer solution B. The third buffer solution C contains two buffer components selected from the group consisting of ammonium bicarbonate, ammonium hydroxide, formic acid, and acetic acid. The third buffer solution C has different buffer components than the second buffer solution B and the first buffer solution A. The first viral vector and the second viral vector can be separated so that the first viral vector and the second viral vector elute off the anion exchange column at different times. The first viral vector and the second viral vector can be detected with a detector.

In regard to the any of the third aspects, the controlling the proportion for each of the first buffer solution A, the second buffer solution B, and the third buffer solution C, can be controlled as a function of time to form a pH gradient.

In regard to any of the third aspects, the first buffer solution A, the second buffer solution B, and the third buffer solution C each do not include non-volatile buffer salts dissolved in the liquid.

In regard to any of the third aspects, the combining the first buffer solution A, the second buffer solution B, and the third buffer solution C includes mixing the first buffer solution A, the second buffer solution B, and the third buffer solution C, in a mixer before the first buffer solution A, the second buffer solution B, and the third buffer solution C, solution are flowed into the anion exchange column.

In regard to the any of the aspects, the first viral vector includes a first capsid configured to contain the targeted genetic material and the first capsid contains the targeted genetic material. The second viral vector includes a second capsid configured to contain the targeted genetic material and the second capsid contains i) essentially no genetic material or ii) the non-targeted genetic material.

In regard to the any of the aspects, at least a portion of the targeted genetic material is different than the non-targeted genetic material. For example, a sequence of nucleotides on the targeted genetic material is not present on the non-targeted genetic material. The targeted genetic material can have a predetermined sequence of nucleotides or be a particular gene that causes a host to have a desired property should the host incorporate the targeted genetic material. The non-targeted genetic material can have a different sequence of nucleotides than the targeted genetic material and would not cause the host to express the desired property should the host incorporate the non-targeted genetic material.

In regard to the any of the aspects, the non-targeted genetic material can correspond to a truncated sequence of nucleotides compared to the targeted genetic material. The non-targeted genetic material can have a subset of the sequence of nucleotides of the targeted genetic material that was caused by a truncation process.

In regard to the any of the aspects, the first vector has a first pI and the second vector has a second pI, wherein the first pI and the second pI are different. The first vector and the second vector each comprise a protein shell that have a substantially identical primary protein structure.

In regard to the any of the first aspects, the first buffer solution A and the second buffer solution B, each consist of only volatile buffer salts dissolved in a liquid. The volatile buffer salts are configured to form a gas at a temperature range of 18° C. to 120° C. at one atmosphere.

In regard to the any of the second aspects, the first buffer solution A, the second buffer solution B, the third buffer solution C, and the fourth buffer solution D each consist of only volatile buffer salts dissolved in a liquid. The volatile buffer salts are configured to form a gas at a temperature range of 18° C. to 120° C. at one atmosphere.

In regard to the any of the third aspects, the first buffer solution A, the second buffer solution B, and the third buffer solution C each consist of only volatile buffer salts dissolved in a liquid. The volatile buffer salts are configured to form a gas at a temperature range of 18° C. to 120° C. at one atmosphere.

In regard to the any of the aspects, the detector is selected from the group consisting of a mass spectrometer, a fluorescence detector, an ultraviolet-visible spectrophotometer, a multiangle light scattering spectrophotometer, and a combination thereof.

In regard to the any of the aspects, the anion exchange column includes a substrate including a crosslinked copolymer of ethylvinylbenzene and divinylbenzene. A coating of a neutral hydrophilic polymer can be on the substrate. Grafted quaternary ammonium groups can be attached to the coating.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention (wherein like numerals represent like elements).

DETAILED DESCRIPTION OF EMBODIMENTS

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention. As used herein, the terms "about" or "approximately" for any numerical values or ranges indicate a suitable dimensional tolerance that allows the part or collection of components to function for its intended purpose as described herein.

A volatile pH gradient mobile phase system for anion exchange (AEX) separation is described for separating full and empty viral vectors. After the separation, a mass spectrometry (MS) detector can detect the separated viral vectors and provide enhanced information compared to other detectors such as absorbance or fluorescence. For instance, unlike absorbance or fluorescence detectors, MS provides mass data and has the ability to generate fragmentation data for structural insights. However, MS compatible buffers typically require that the buffer components are volatile so that the ionization module of a MS does not get clogged or contaminated. Buffering components include materials (sometimes referred to as salts) that are resistant to pH change especially in helping hold the pH to be within plus or minus one pH unit of the pKa value. Buffering components are typically weak acids or weak bases. A weak acid and a weak base each do not fully ionize when dissolved in water. Weak acids typically have a pH between 3 and 6. Weak bases typically have a pH between 7 and 10.

In an example, a method is described to separate and characterize empty vs full viral particles using a pH gradient. A salt gradient may be used to partially separate empty and full viral particles. However, a salt gradient method typically uses relatively high salt concentrations and does not allow one to analyze these vectors using MS for helping characterize the viral particles. As described herein, a mobile phase system that utilizes mass spectrometry compatible components (i.e., volatile buffer salts) to generate a pH gradient can allow the separation of empty and full viral particles and subsequent characterization by MS.

In another example, the MS detector can provide accurate mass data of the whole viral particle. The volatile buffer system can provide a pH range ranging from 9.2 to 2.5 for eluting the viral particles on the anion exchange column. The volatile buffer system can have a relatively low total buffer concentration (e.g., Mobile phase A and B together), such as for example, ranging from about 10 mM to about 150 mM, preferably range from about 10 mM to about 100 mM, and more preferably ranging from 20 mM to 100 mM. Even when using volatile buffer salts, it is desirable to use relatively low total buffer concentration to reduce the risk of clogging or contaminating MS systems. Mobile phase A that can have 20 mM ammonium bicarbonate and 15 mM ammonium hydroxide has a total buffer concentration of 55 mM (35 mM ammonium ions +20 mM bicarbonate ions). In calculating the total buffer concentration, the hydroxide does not count as a buffer component. Mobile phase B that can have 30 mM acetic acid and 15 mM formic acid has a total buffer concentration of 45 mM (30 mM acetic acid +15 mM formic acid). When mixing mobile phase A and B together during a separation, the total buffer concentration (e.g., both A and B) can be less than 100 mM to help maintain sensitivity in the MS. This mobile phase system is not limited to MS detection and can be used in combination with UV and fluorescence detectors.

The process of filling an empty viral vector with genetic material can cause the protein shell of the viral particle to have a conformational change to reveal new ionic sites that change the pI at the surface of the protein shell. For reference, genetic material may include a gene, DNA, RNA, oligonucleotides, DNA/RNA including modified nucleotides, and DNA/RNA including nucleotide analogues. As such, the pI of empty vial particles would be different than the pI of viral particles filled with genetic material. The difference in pI can cause the empty viral particles and filled viral particles to elute off an anion exchange column at different retention times. The method described herein uses a pH gradient on a relatively short column (e.g., 50 mm length cylinder) and allows samples to be characterized in regard to the proportion of empty viral particles. The chromatographic resolution for the pH gradient separation described herein has been found to be generally superior than salt gradient elution methods (with non-volatile buffer salts) that are not MS compatible. Detection of full and empty particles can be achieved using the UV absorbance ratio at 260/280 nm, in which a full particle has a higher absorbance at 260 nm due to the incorporated genetic material. The analysis can be fast and be completed using a short gradient of under 10 minutes. Alternatively, a fluorescence detector can be used to achieve higher sensitivity and avoid interference of the genetic material signal with the protein signal that is seen in UV absorption measurements using 280 nm.

In an example, full and empty viral particles can be introduced directly into the MS from the chromatography column. The information generated from the MS analysis on-line can provide added information in addition to the ratio of the full and empty capsid provided by UV or fluorescence detection.

In addition to full and empty viral particles, a first viral vector can contain the targeted genetic material and the second viral vector can contain a non-targeted genetic material. Viral vectors can be an AAV vector that is derived from an adeno-associated virus serotype. The targeted genetic material can be a predetermined gene that has a desirable property that can be transferred to the host after infection by the viral vector. The non-targeted material is different than the targeted genetic material, and in some instances, can be a truncated version of the targeted genetic material (e.g., the targeted genetic material with a portion removed). For example, the non-targeted material can have a different sequence of nucleotides (DNA or RNA) compared the targeted material where the non-targeted material does not cause the desirable property to be expressed in the host. The first viral vector can have a different pI than the second viral vector because the non-targeted genetic material causes a different conformation change to the protein shell. Based on the different pI values, the first and second viral vectors can be separated with an ion exchange column. It is worthwhile to note that the terms "first" and "second" with respect to viral vectors are used for reference and do not necessarily provide the elution order in which they elute off a chromatography column.

The following will describe a buffer kit that provides a pH gradient. The pH gradient represents changing pH values based on a function of time for at least a pH range of about pH 9 to about pH 3. Applicant believes that a pH gradient with ion exchange chromatography will provide an improved method for characterizing proteins such as viral vectors.

Figure 2A:
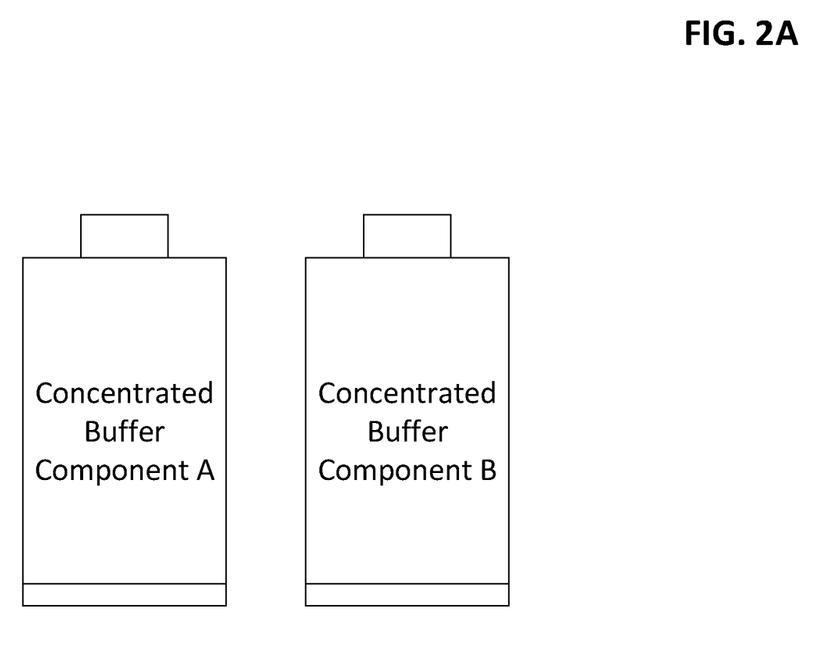
FIG. 2A illustrates a first sealed container that contains buffer components A and a second sealed container that contains buffer components B.
Figure 2B:
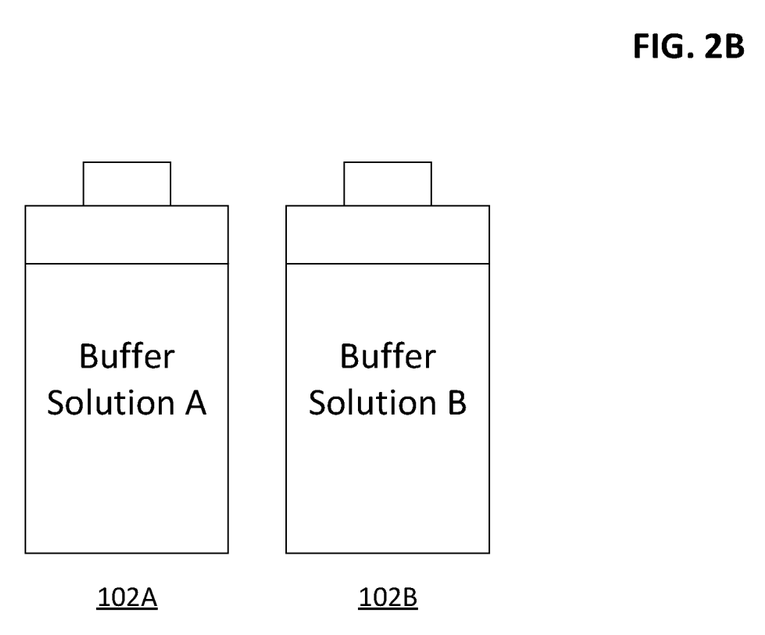
FIG. 2B illustrates a first container that contains first buffer solution A and a second container that contains second buffer solution B.

As an example, the buffer kit can include a buffer solution A and a buffer solution B. Note that an eluent solution, buffer solution, combined buffer solutions, or mobile phase can be a solution that is used to elute a sample from an ion exchange stationary phase. The buffer solutions A and B (102A and 102B) may be packaged into a respective liquid container or vial, as shown in FIG. 2B. To reduce the shipping weight and enhance long term stability, the buffer components for buffer solution A and the buffer components for buffer solution B can be packaged in a concentrated form in a sealed vial with a removable cap, as shown in FIG. 2A. Under circumstances where the buffer components are volatile, the stability is improved when they are stored in a sealed container. Once a test is initiated, fresh buffer solutions A & B can be prepared daily or periodically by adding a predetermined amount of water to concentrated buffer component container A and to concentrated buffer component container B. It should be noted that the buffer kit described herein should not be limited to only two buffer solutions and that buffer kits can be implemented using additional types of liquids, solutions, or other buffer solutions. For example, container C and D may be used where container C could contain water and container D could contain another volatile buffer salt or organic solvent.

Regarding the first buffer solution A, it may include at least two buffer salts dissolved in a liquid. All of the buffer salts in first buffer solution A are volatile so that they form a gas at a temperature range from about 25° C. to about 120° C. at about one atmosphere (e.g., +/−10% of 101.325 kPa or 14.7 psi) and preferably range from about 25° C. to about 120° C. at about one atmospheric pressure, which corresponds to typical conditions for inputting a liquid sample into a MS using atmospheric electrospray. When using buffer solutions with MS, the buffers typically use volatile buffer salts so that residue or salts do not clog the ionization needle, input ports, or generally contaminate the ionization module of a MS. Buffer solution A can include ammonium bicarbonate and ammonium hydroxide. Buffer solution B can include acetic acid and formic acid.

The first buffer solution A may have a first pH ranging from about 8 to about 10, and total buffer salt concentration ranging from about 5 to about 100 millimolar and preferably ranging from about 20 to about 60 millimolar. The second buffer solution B may have a second pH ranging from about 1.8 to about 3.8 and total buffer salt concentration ranging from about 5 to about 100 millimolar and preferably ranging from about 20 to about 60 millimolar. The buffer salt concentration of the first buffer solution A and the second buffer solution B can be selected so that the buffering capacity is greater than both the sample containing viral vectors and the anion exchange chromatography column. An example of the buffer salt concentration values for the first buffer solution A is 20 mM ammonium bicarbonate and 15 mM ammonium hydroxide and for the second buffer solution B is 30 mM acetic acid and 15 mM formic acid.

The first buffer solution A can be mixed with the second buffer solution B to create a decreasing pH gradient. The first buffer solution can have a first pH that is greater than the second pH of the second buffer solution. The first buffer solution A may include ammonium bicarbonate as the first buffer salt and ammonium hydroxide as the second buffer salt. Ammonium pKa of 9.2 and bicarbonate has a pKa of 6.1. The second buffer solution B may include acetic acid as the third buffer salt and formic acid as the fourth buffer salt. Acetic acid has a pKa of 4.8 and formic acid has a pKa of 3.8. It should be noted that all pKa values stated herein are stated with respect to 25° C. unless explicitly stated to be at a different temperature.

Figure 1:
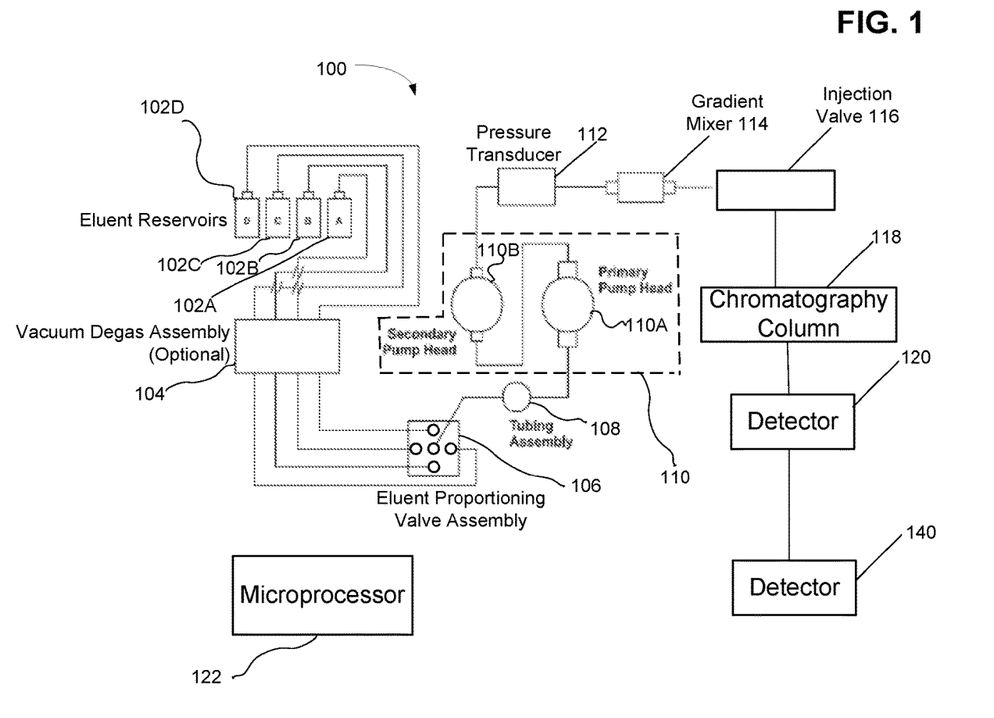
FIG. 1 illustrates a schematic of a chromatography system configured to perform a gradient elution with up to four different mobile phase reservoirs.

Now that the buffer kit has been described, the following will describe a chromatographic system for use with the buffer kit that can generate a pH gradient for separating viral vectors. FIG. 1 illustrates a schematic of a chromatography system 100 configured to perform an isocratic elution or a gradient elution with up to four different mobile phase types. Chromatography system 100 can include four mobile phase reservoirs (102A, 102B, 102C, 102D), an optional degas assembly 104, an eluent proportioning valve assembly 106, a tubing assembly 108, a pump 110, a pressure transducer 112, a gradient mixer 114, an injection valve 116, a chromatography column 118, a detector 120, another detector 140, and a microprocessor 122.

Pump 110 can be configured to pump a liquid from one or more reservoirs through system 100. The pumped liquid may flow through an optional degas assembly 104, and then to eluent proportioning valve assembly 106. A predetermined proportion of liquid can be extracted from each of the four mobile phase reservoirs (102A, 102B, 102C, 102D) using eluent proportioning valve assembly 106 and transmitted to tubing assembly 108 and then pump 110. As an example, mobile phase reservoirs 102A and 102B can be used for buffer solution A and buffer solution B, respectively, for a gradient elution while mobile phase reservoirs 102C and 102D are not used. Pump 110 includes a primary pump head 110A and a secondary pump head 110B. The eluent proportioning valve assembly 106 can direct pump 110 to draw on one of the four mobile phase reservoirs for a predetermined time period and then switch to another mobile phase reservoir. Typically, the pump will draw upon each of the selected mobile phase types at least once during a piston cycle to form a plurality of adjoining solvent volumes. For example, four mobile phase reservoirs (102A, 102B, 102C, 102D) can be used for the pH gradient elution. This will initially form a heterogeneous solvent volume (unmixed) containing liquid volume A, liquid volume B, liquid volume C, and liquid volume D. Note that solvent volumes A, B, C, or D can be referred to as a plug of liquid that flows through a conduit such that there is not complete homogenization between the four plugs. Solvent volumes A, B, C, or D can be in an adjoining and serial relationship. The proportion of solvent volumes A, B, C, or D depends on the timing in which eluent proportioning valve assembly 106 draws on a particular reservoir. The heterogeneous solvent volume is outputted from pump 110 and corresponds to an outputted solvent from one pump cycle. Subsequent to pump 110, the heterogeneous solvent volume can be mixed in gradient mixer 114. Note that the proportion of solvent volumes A and B can change with time to form a pH gradient elution and that solvent reservoirs C and D are not used. Although pump 110 is shown as a ternary pump configured to be in a low pressure gradient format, the pump could also be a binary pump configured to be in a high pressure gradient format.

The output of pump 110 serially flows to pressure transducer 112, mixing device 114, injection valve 116, chromatography column 118, detector 120, and then to another detector 140. Pressure transducer 112 can be used to measure the system pressure of the mobile phase being pumped by pump 110. Injection valve 116 can be used to inject an aliquot of a sample into an eluent stream. Chromatography column 118 can be used to separate various matrix components present in the liquid sample from the analytes of interest. An output of chromatography column 118 can be fluidically connected to detector 120, and then to another detector 140. Detectors 120 and 140 can be in the form of an ultraviolet-visible spectrophotometer (UV) to monitor an absorbance of incident light at a predetermined wavelength as a function of time, a fluorescence detector (FLD), evaporative light scattering detector, multiangle light scattering detector (MALS), a mass spectrometer, and a combination thereof. MALS is a technique for measuring the light scattered by a compound into a multitude of angles. MALS can provide a determination of the molar mass and the average size of molecules in solution, by detecting how the compounds scatter light.

For example, a non-destructive detector can be used in an upstream detector 120 such as ultraviolet-visible spectrophotometer or fluorescence detector to identify and full or empty capsids Next, the sample can then be inputted into another detector 140 (downstream of detector 120), which can be a destructive detector such as MS to further characterize the sample.

Chromatography column 118 can separate one or more analytes of a sample that is outputted at different retention times. For example, chromatography column 118 can be in the form of an anion exchange column (with either weak or strong anion exchange sites). The resin inside a column can include a substrate, a coating on the substrate, and a grafted anion exchange group attached to the coating. The substrate can be a crosslinked copolymer of ethylvinylbenzene and divinylbenzene. The coating can be a neutral hydrophilic polymer on a surface of the substrate. The grafted anion exchange group can be quaternary ammonium groups (or tertiary amine groups) attached to the coating. A commercially available anion exchange column that can be suitable for use with the methods described herein is the Thermo Scientific™ ProPac™ SAX column (strong anion exchange, 10 micron diameter particle size), Thermo Scientific™ DNAPac™ PA100 column, Thermo Scientific™ DNAPac™ PA200 column (non-porous substrate particle with quaternary ammonium functionalized nanobeads), Dionex™ Ionpac™ AS32-Fast column (supermacroporous ethylvinylbenzene polymer cross-linked with divinylbenzene having alkanol quaternary ammonium groups), Thermo Scientific™ ProSwift™ SAX-1S column, Thermo Scientific™ DNASwift™ SAX-1S Oligonucleotide column, YMC BioPro™ IEX QA column (hydrophilic porous polymer beads with quaternary ammonium groups), YMC BioPro™ IEX QF column (hydrophilic non-porous polymer beads with quaternary ammonium groups), and Waters Protein-Pak Hi Res Q (non-porous polymethacrylate particle substrate).

Microprocessor 122 can include a memory portion and be used to control the operation of chromatography system 100. Microprocessor 122 may either be integrated into chromatography system 100 or be part of a personal computer that sends a signal to communicate with chromatography system 100. Microprocessor 122 may be configured to communicate with and control one or more components of chromatography system such as pump 110, eluent proportioning valve 106, injection valve 116, and detectors 120 and 140. Memory portion can include software or firmware instructions on how to control pump 110, eluent proportioning valve 106, injection valve 116, and detectors 120 and 140.

Now that the chromatography system has been described, the following will describe a method of separating a liquid sample containing viral vectors. The liquid sample can be a liquid aliquot obtained from a manufacturing batch of viral vectors. The viral vector can be in the form of a virus that has a particular genetic material that can efficiently transport the particular genetic material into a cell infected by the virus. As an example, the infected cell could incorporate the genetic material from the virus and under certain circumstances cause the infected cell to have improved immunity to a particular disease.

As an example, the liquid sample would contain viral vectors where each one contains a copy of the targeted genetic material. However, in practice, there are some proportion of viral vectors that are empty and do not contain genetic material. A viral vector that is essentially free of genetic material can have an amount genetic material that is not measurable using a detector. Alternatively, a viral vector can have a truncated genetic material or a different genetic material that is not the targeted genetic material.

After injecting the liquid sample onto the anion exchange chromatography column 118 with an injection valve 116, the mobile phase can continue to be pumped with pump 110 and flow the mobile phase into the anion exchange column 118 for eluting components of the sample. The mobile phase can include a buffer solution A and a buffer solution B at various proportions as a function of time. Buffer solution A can be in eluent reservoir 102A that contains ammonium bicarbonate and ammonium hydroxide. Buffer solution A can have a pH value that ranges from 8 to 10, and preferably is 9. For buffer solution A, the ammonium bicarbonate concentration can range from 5 to 50 mM, and the ammonium hydroxide concentration can range from 5 to 50 mM. Buffer solution B can be in eluent reservoir 102B that contains acetic acid and formic acid. Buffer solution B can have a pH value that ranges from 1.8 to 3.8, and preferably is 2.8. For buffer solution B, the acetic acid concentration can range from 5 to 50 mM, and the formic acid concentration can range from 5 to 50 mM. The proportions of buffer solution A and a buffer solution B can be varied as a function of time by using eluent proportioning valve assembly 106.

As an example, the buffer solution A and the buffer solution B, each consist of only volatile buffer salts dissolved in a liquid. The volatile buffer salts form a gas at a temperature range of 25° C. to 120° C. at about one atmosphere. The use of volatile buffer salts causes them to go into the gas phase when the buffer solutions are sprayed with an emitter column to form charged gas ions. Buffer solution A and the Buffer solution B, each do not include non-volatile buffer salts dissolved in the liquid. If non-volatile buffer salts that are sprayed with an emitter column, they can form a residue that clogs and/or interferes with the electrospray ionization process. In addition, the use of non-volatile buffer salts in the mobile cause a need to more frequently clean a MS when coupled to the effluent of a liquid chromatography column.

As the liquid sample flows through the anion exchange chromatography column, a first viral vector that contains genetic material is separated from a second viral vector that is empty or contain essentially no genetic material. This causes the first viral vector and the second viral vector to elute off the anion exchange column at different times. The first viral vector and the second viral vector both include a protein shell, which can be referred to as a capsid. The first viral vector can include a first capsid configured to contain the genetic material and the first capsid is essentially free of the genetic material. The second viral vector can include a second capsid configured to contain the genetic material and the second capsid contains the genetic material. The protein shell of the first vector and the second vector can be substantially identical where the primary protein structure is at least 95% identical, and preferably at least 99% identical.

Applicant believes that the incorporation of genetic material caused a change in at least a surface charge of the first vector relative to the second vector which does not contain the genetic material. Alternatively, it is possible that the incorporation of genetic material caused a change in accessibility to the stationary phase for the first vector relative to the second vector which does not contain the genetic material. This change in surface charge caused the first viral vector and the second viral vector to have different affinities to the anion exchange chromatography column and caused the first viral vector and the second viral vector to be eluted off the column with different retention times. In addition, the incorporation of genetic material is believed to have caused a change in pI for the first vector relative to the second vector which does not contain the genetic material. This change in pI causes the first viral vector and the second viral vector to be eluted off the column with different retention times. As an example, a difference in pI between the first viral vector and the second viral vector can range from 0.1 to 0.5 is sufficient to provide sufficient resolution in separating the two viral vectors from each other. Under certain circumstances, the difference in pI can be more than 0.5.

In addition to empty versus full vectors, Applicant believes that the incorporation of targeted genetic material into a first capsid versus the incorporation of a different non-targeted genetic material into a second capsid can result in a change in at least a surface charge of the second vector relative to the first vector. In addition, it is possible that the incorporation of non-targeted genetic material caused a change in accessibility to the stationary phase for the second vector relative to the first vector which does contain the targeted genetic material. The targeted genetic material is different than the non-targeted genetic material. This change in surface charge can cause the first viral vector and the second viral vector to have different affinities to the anion exchange chromatography column and cause the first viral vector and the second viral vector to be eluted off the column with different retention times. In addition, the incorporation of non-targeted genetic material is believed to have caused a change in pI for the second vector relative to the first vector which contains the targeted genetic material. This change in pI causes the first viral vector and the second viral vector to be eluted off the column with different retention times. As an example, a difference in pI between the first viral vector and the second viral vector can range from 0.1 to 0.5 is sufficient to provide sufficient resolution in separating the two viral vectors from each other. Under certain circumstances, the difference in pI can be more than 0.5.

After separating the first viral vector and the second viral vector, they can be eluted off the column and then detected with a first detector 120. Typically, the first detector 120 is a non-destructive detector such as UV-VIS or FLD. Subsequent to the first detector 120, the first viral vector and the second viral vector can then flow towards another detector 140. As an example, the first viral vector and the second viral vector can flow towards another detector 140 as intact proteins. This way the viral vectors can be characterized with a MS with the native state of the proteins.

Example 1

The following will describe the set-up of chromatographic system 100 (Thermo Scientific Ultimate 300 BioRS, Germering, Germany) that was similar to FIG. 1. Pump 110 was a HPLC pump (LPG-3400RS, Thermo Scientific, Germering, Germany.) that was set to a flow rate of 1.75 mL/minute and a pressure of 2600 PSI. Injection valve 116 (WPS-3000TBRS, Thermo Scientific, Germering, Germany) was configured to have a 20 microliters sample loop. Chromatographic separation device 118 (ProPac SAX-10, 10 µm, 4×50 mm from Thermo Scientific Dionex, Sunnyvale, California, U.S.A.) was a strong anion exchange column suitable for use in separating proteins. The strong anion exchange resin has a particle diameter of 10 microns and the column has an inner diameter of 4 mm and a length of 50 mm. Chromatographic system 100 was configured to heat the chromatographic separation device 118 to 30° C. Detector 120 (DAD-3000RS, Thermo Scientific, Germering, Germany) was in the form of a UV-VIS spectrophotometer and set to the wavelengths of 260 nanometers and 280 nanometers or detector 120 was in the form of a fluorescence detector (5078.0020, Thermo Scientific Dionex, Germering, Germany) and set to absorbance wavelength of 280 nm and emission wavelength of 330 nm.

Buffer solution A was prepared to have the following concentrations 20 mM ammonium bicarbonate and 15 mM ammonium hydroxide at pH 9.1. Buffer solution B was prepared to have 30 mM acetic acid and 15 mM formic acid at pH 2.8.

Pump 110 was configured to provide a gradient mobile phase using a proportion of the buffer solution A and buffer solution B. The gradient was configured to provide the following parameters shown in Table 1.

TABLE 1

| Time (minutes) | % A | % B |
| --- | --- | --- |
| 0 | 80 | 20 |
| 0.5 | 80 | 20 |
| 15.5 | 30 | 70 |
| 15.5 | 0 | 100 |
| 16 | 0 | 100 |
| 16 | 80 | 20 |
| 30 | 80 | 20 |

Figure 3:
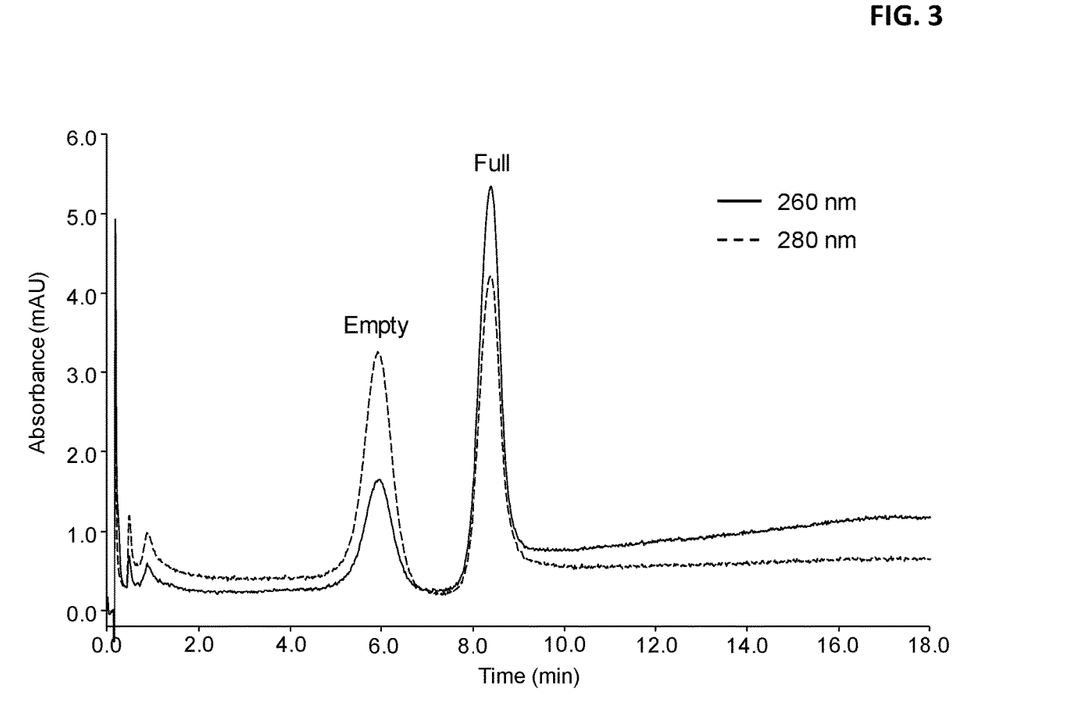
FIG. 3 illustrates a chromatogram for analyzing an AAV8 sample containing a first type of capsids contained genetic material and a second type of capsids did not contain genetic material with an anion exchange chromatography column. One trace monitors the effluent at 260 nm and the other trace monitors the effluent at 280 nm.

FIG. 3 is a chromatogram of an AAV8 sample (generated using Baculovirus-Sf9 insect cell expression system by Virovek, Inc.) containing a mixture of full and empty viral vectors where the detector was monitoring at 260 nm and 280 nm. For both wavelengths, the empty viral vector eluted at about 6 minutes and the full viral vector eluted at about 8.5 minutes.

Example 2

The following will describe the testing of AAV9 viral vector samples using chromatographic system 100 with similar conditions as described in Example 1. In this example, the gradient was configured to provide the following parameters shown in Table 2.

TABLE 1

| Time (minutes) | % A | % B |
|---|---|---|
| 0 | 100 | 0 |
| 0.5 | 100 | 0 |
| 15.5 | 20 | 80 |
| 15.5 | 0 | 100 |
| 16 | 0 | 100 |
| 16 | 100 | 0 |
| 30 | 100 | 0 |

Figure 4:
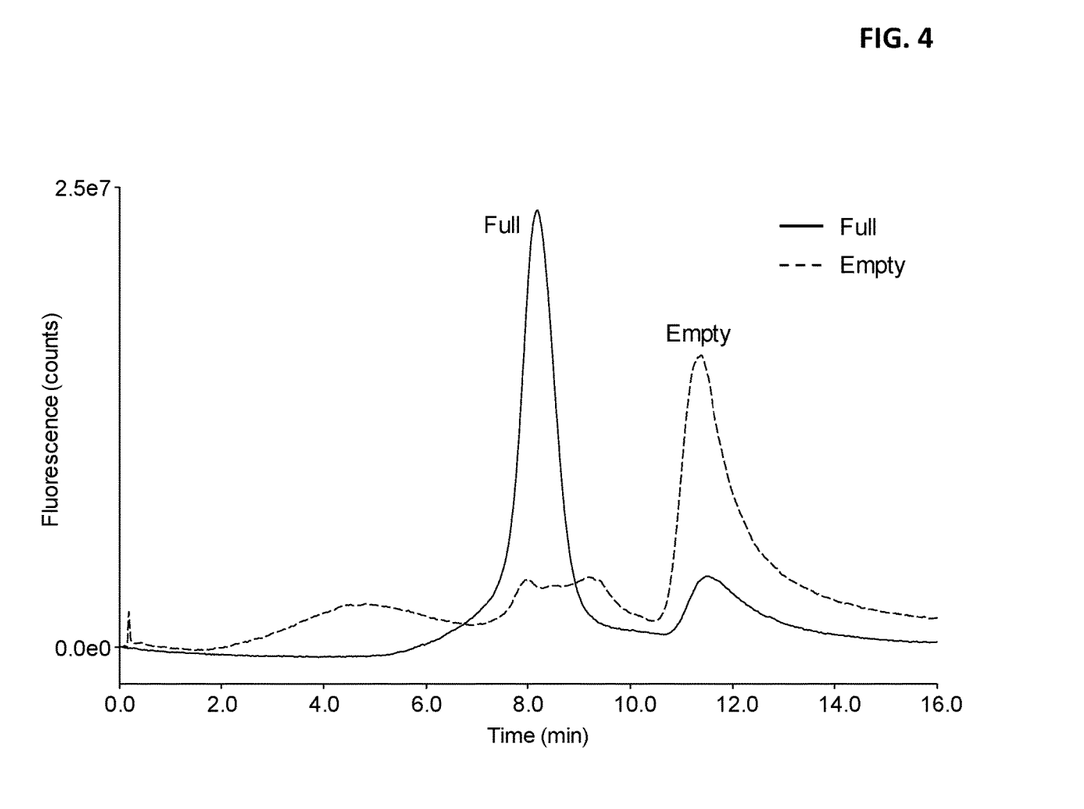
FIG. 4 illustrates two chromatograms for analyzing two AAV9 samples where one sample had capsids filled with genetic material and another sample had capsids that were empty with an anion exchange chromatography column.

In this example, the injection volume was 2 microliters and the detector was a FLD (Excitation 280 nm/Emission 330 nm). FIG. 4 showed two chromatograms of two different AAV9 samples (generated using Baculovirus-Sf9 insect cell expression system by Virovek, Inc.) where one sample corresponds to predominantly full viral vectors containing genetic material and the other sample corresponds to empty viral vectors containing essentially no genetic material. The empty viral vector elutes at about 11.5 minutes and the full viral vector elutes at about 8.25.

While preferred embodiments of the present invention have been shown and described herein, it will be apparent to those skilled in the art that such embodiments are provided by way of example only. Numerous variations, changes, and substitutions will now occur to those skilled in the art without departing from the invention. While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well.

What is claimed is:

1. A method of eluting separately adeno-associated viral (AAV) vectors, the method comprising:
    a) flowing a mobile phase into an anion exchange column, wherein the mobile phase comprises a mixture of a first buffer solution A having a high pH value and a second buffer solution B having a low pH value, wherein initially the concentration of the first buffer solution A is higher than the concentration of second buffer solution B;
    b) flowing a liquid sample containing AAV vectors into the anion exchange column, wherein the AAV vectors comprise a first viral vector and a second viral vector, the first viral vector contains a targeted genetic material, and
    the second viral vector contains i) essentially no genetic material or ii) a non-targeted genetic material, wherein the targeted genetic material is different than the non-targeted genetic material;
    c) eluting the first viral vector and the second viral vector at different times by decreasing the concentration of the first buffer solution A and increasing the concentration of the second buffer solution B in the mobile phase thereby creating a decreasing pH gradient in the mobile phase;
    wherein the first viral vector and the second viral vector are detected with a detector coupled to the ion exchange column;
    wherein the first buffer solution A comprises ammonium bicarbonate and ammonium hydroxide, and the second buffer solution B comprises acetic acid and formic acid; and
    wherein the first viral vector has a first pI and the second viral vector has a second pI, wherein the first pI and the second pI are different, wherein the first viral vector and the second viral vector each comprise a protein shell that have a substantially identical primary protein structure.

2. The method of claim 1, wherein the second viral vector contains i) the essentially no genetic material.

3. The method of claim 1, wherein the second viral vector contains ii) the non-targeted genetic material.

4. The method of claim 1, wherein the non-targeted genetic material corresponds to a truncated sequence of nucleotides compared to the targeted genetic material.

5. The method of claim 1, wherein the first buffer solution A and the second buffer solution B, each consist of only volatile buffer salts dissolved in a liquid, wherein the volatile buffer salts are configured to form a gas at a temperature range of 18° C. to 120° C. at one atmosphere.

6. The method of claim 1, wherein the detector is selected from the group consisting of a mass spectrometer, a fluorescence detector, an ultraviolet-visible spectrophotometer, a multiangle light scattering spectrophotometer, and a combination thereof.

7. The method of claim 1, wherein the anion exchange column comprises:
    a substrate including a crosslinked copolymer of ethylvinylbenzene and divinylbenzene;
    a coating of a neutral hydrophilic polymer on the substrate; and
    grafted quaternary ammonium groups attached to the coating.

8. The method of claim 1, wherein the flowing the mobile phase into the anion exchange column comprises:
    pumping the first buffer solution A from a first reservoir; and
    pumping the second buffer solution B from a second reservoir;
    wherein the mixture of the first buffer solution A and the second buffer solution B is formed by combining the pumped first buffer solution A and the pumped second buffer solution B.

9. The method of claim 8, wherein the combining the pumped first buffer solution A and the pumped second buffer solution B comprises:
    mixing the pumped first buffer solution A and the pumped second buffer solution B in a mixer before the pumped first buffer solution A and the pumped second buffer solution B are flowed into the anion exchange column.

10. The method of claim 1, wherein the AAV vectors is AAV8 or AAV9.

11. The method of claim 1, wherein the detector includes a mass spectrometer.

* * * * *

UNITED STATES PATENT AND TRADEMARK OFFICE
CERTIFICATE OF CORRECTION

| | |
|---|---|
| PATENT NO. | : 11,821,000 B2 |
| APPLICATION NO. | : 17/094522 |
| DATED | : November 21, 2023 |
| INVENTOR(S) | : Kenneth George Cook et al. |

It is certified that error appears in the above-identified patent and that said Letters Patent is hereby corrected as shown below:

On the Title Page

In Column 1, item (72), under Inventors, Line 1, delete "Nothumberland" and insert -- Northumberland --, therefor.

Signed and Sealed this
Second Day of January, 2024

Katherine Kelly Vidal
*Director of the United States Patent and Trademark Office*